Figure 1:
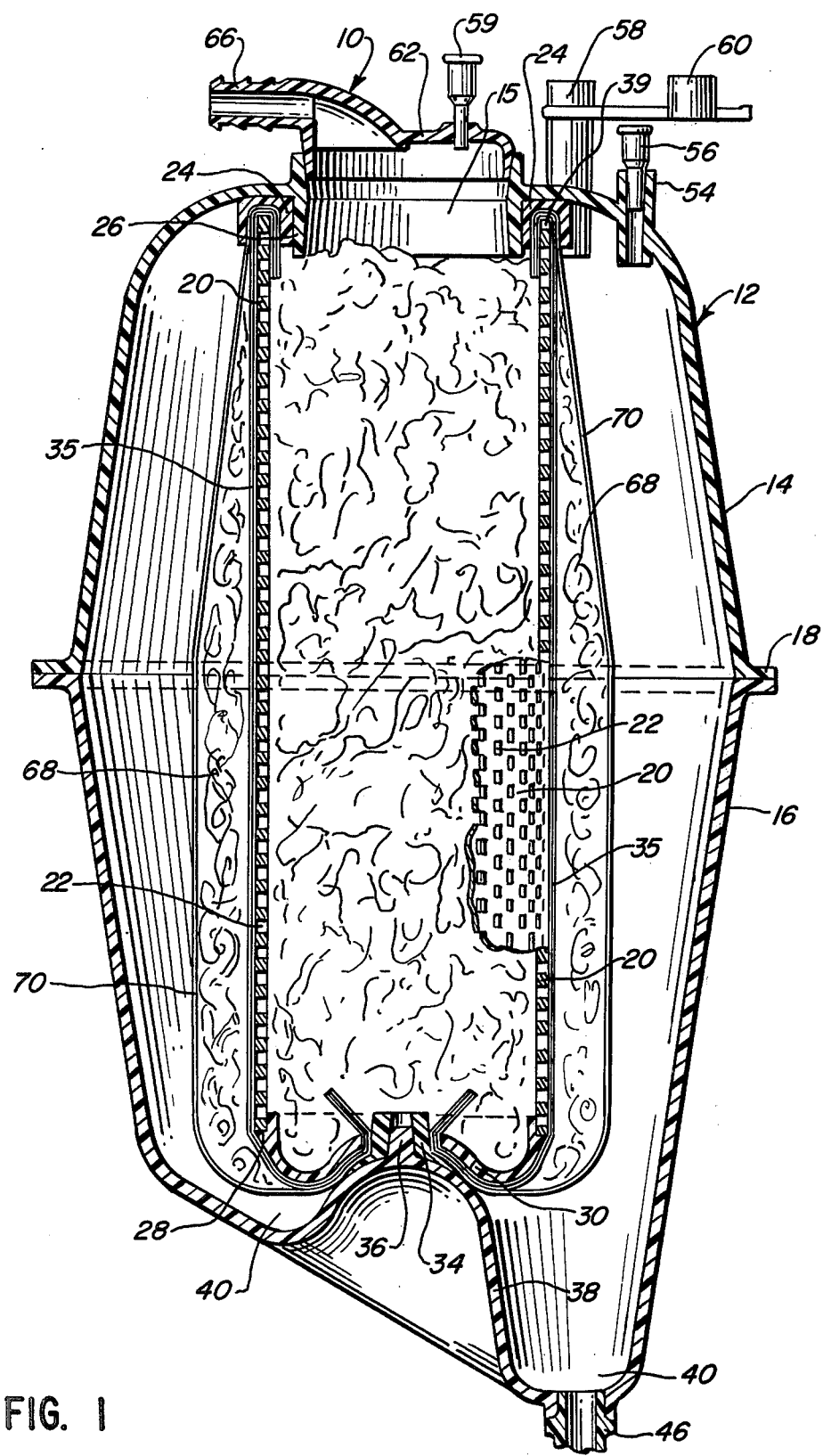

United States Patent [19]

Munsch et al.

[11] 4,208,193
[45] Jun. 17, 1980

[54] CARDIOTOMY RESERVOIR HAVING TWO-STAGE DEFOAMING MEANS

[75] Inventors: John M. Munsch, Libertyville; Ludwig Wolf, Jr., Crystal Lake, both of Ill.

[73] Assignee: Baxter Travenol Laboratories, Inc., Deerfield, Ill.

[21] Appl. No.: 959,113

[22] Filed: Nov. 9, 1978

[51] Int. Cl.² .................................................. B01D 19/00
[52] U.S. Cl. .......................................... 55/36; 55/178; 210/65; 210/323 T; 210/436; 210/457; 210/DIG. 23
[58] Field of Search .......................... 55/178; 128/415; 210/322, 338, 436, 457, DIG. 23

[56] References Cited

U.S. PATENT DOCUMENTS

| | | | |
|---|---|---|---|
| 3,891,416 | 6/1975 | Leonard et al. | 55/178 |
| 4,054,523 | 10/1977 | Ingenito et al. | 210/436 X |
| 4,073,622 | 2/1978 | Luppi | 55/178 X |

Primary Examiner—Charles N. Hart
Assistant Examiner—Richard W. Burks
Attorney, Agent, or Firm—Paul C. Flattery; Garrettson Ellis

[57] ABSTRACT

A blood reservoir comprises a rigid casing and a perforated tubular member positioned within the casing and extending between the edges thereof. An inlet aperture is at a position at the upper end of the reservoir in communication with the bore of the tubular member while an outlet aperture is positioned adjacent the bottom of the casing exterior to the tubular member. The bore of the tubular member contains first blood-defoaming means, and the tubular member carries a blood filter. In accordance with this invention, second blood defoaming means are positioned about the exterior of the tubular member to dissipate the fine bubbles without interference from the larger bubbles, which have been previously removed by passage through the first blood defoaming means.

9 Claims, 1 Drawing Figure

CARDIOTOMY RESERVOIR HAVING TWO-STAGE DEFOAMING MEANS

BACKGROUND OF THE INVENTION

Cardiotomy reservoirs are currently used in major surgical procedures, such as open heart surgery, for receiving blood from a cardiotomy sucker and other sources, for defoaming the blood, filtering out debris, and returning it to the patient.

In U.S. Application Ser. No. 901,323 filed May 30, 1978, by Thomas W. Crockett, et al. and entitled "Improved Cardiotomy Reservoir", a reservoir for blood is disclosed, having a rigid casing and a perforated tubular member positioned within the casing and extending between the ends thereof. Blood defoaming material is positioned within the tubular member, and a filter is carried by the tubular member so that blood clots and larger bubbles cannot escape from the interior of the filter member to the exterior.

Other designs of cardiotomy reservoirs are known, for example, a cardiotomy reservoir similar to that disclosed in U.S. Pat. No. 3,993,461, its predecessor in design being as disclosed in U.S. Pat. No. 3,891,416. In both of these cardiotomy reservoirs, a hollow casing is provided in which a tubular member is positioned within the casing and extends between the ends thereof. Blood enters the bottom of the tubular member rising upwardly until it passes out of an aperture to the exterior of the tubular member.

In accordance with this invention, the above described type of cardiotomy reservoir is improved by the use of a double stage defoaming structure.

As in the previously cited patent application, the defoaming sponge within the tubular member may be surrounded by a fine weave filter netting, which confines large gas bubbles to the region containing the first defoaming sponge material. Small bubbles, however, may pass through the filter screen.

In the structure of this invention, those small bubbles which do pass through the filter screen to the area which is outside of the tubular member encounter a second defoaming sponge, where they also are broken down. Unlike the situation in the first defoaming means, the second stage can dissipate the fine bubbles without interference from the large bubbles, which can tend to create small bubbles and inhibit their dissipation.

Also, the structure of this invention may be adapted so that small bubbles which are formed or otherwise reside within the reservoir outside of the tubular member and fine weave filter netting may easily enter into contact with the second defoaming means for further bubble removal.

DESCRIPTION OF THE INVENTION

There is disclosed herein a blood reservoir which comprises a rigid casing, a perforated tubular member positioned within the casing and extending between the ends thereof, and inlet aperture means positioned at the upper end of the reservoir in communication with the bore of the tubular member, to provide fluid communication from the exterior to the bore.

The bore contains first blood defoaming means, while the tubular member carries blood filter means to filter fluid passing through the perforations of the tubular member. An outlet aperture is positioned at the bottom of the casing, exterior to the tubular member.

In accordance with this invention, second blood defoaming means are positioned about the exterior of the tubular member to dissipate fine bubbles without interference from larger bubbles previously removed by the first blood defoaming means.

Preferably, the second blood defoaming means are enclosed in a tubular, coarse-weave cover, capable of allowing small bubbles outside of the cover to pass therethrough into contact with the second blood defoaming means. Thus, bubbles which are generated or otherwise reside exterior to the tubular member and fine weave filter netting can be dissipated with the assistance of the second blood defoaming means.

The first and second blood defoaming means may be separated by the blood filter means, with the filter member being of tubular shape and fine-weave construction. This permits the filter, which is made of generally hydrophilic material, to retain larger bubbles to prevent their passage from the inside to the outside of the filter means. Typically, the tubular, fine-weave filter member may have a pore size of, for example, 120 to 130 microns, and may be made of a nylon material.

Because of the second stage blood defoaming means present in accordance with this invention, a significant improvement in the performance of the cardiotomy reservoir of this invention is provided over those of the prior art.

Referring to the drawings, FIG. 1 is a vertical sectional view of the cardiotomy reservoir of this invention.

Referring to the drawings, the cardiotomy reservoir which is shown herein is similar in its design to the cardiotomy reservoir of the Crockett, et al. patent application No. 901,323, filed May 30, 1978, entitled "Improved Cardiotomy Reservoir", except as otherwise indicated herein.

Cardiotomy reservoir 10 comprises a rigid housing 12 which may be made from a pair of shells 14, 16, sealed together about flanges 18 by radio-frequency sealing, solvent sealing, or the like. Casing 12 may be made of a transparent acrylic plastic or similar material.

Casing 12 encloses a perforated tubular member 20, which may be made out of polyethylene, or other similar plastic, and typically carries numerous perforations 22 so that the walls of the tubular member can pass fluid. The upper end of tubular member 20 is positioned within an annular gasket 24 which may be made out of silicone rubber, and which fits about flange 26 positioned at the end of shell 14 about aperture 15 in a sealing manner.

The lower end of tubular member 20 rests in an annular ledge 28 of a plate 30. Plate 30 is retained by a silicone rubber end plug 34, defining an aperture which surrounds protrusion 36. Protrusion 36 is part of inwardly upstanding hump 38, which is defined at the bottom end of shell 16.

Tubular member 20 carries, preferably about its exterior, a tubular nylon filter screen 35, which may have a mesh size of about 125 microns for filtration of the blood and the retention of debris.

A fine weave filter 35 is folded at its upper end about the upper end of tubular member 20, inside of slot 39 of silicone rubber gasket 24, for frictional retention of the ends of tubular filter 35. At the lower end, filter 35 passes under plate 30, and then fits through the central aperture of plate 30, between the plate and plug 34, for frictional retention. Filter 35 may have a pore size on the order of 120 to 130 microns, specifically 125 microns.

Annular trough 40 is defined about hump 38 in shell 16, and is angularly positioned to define an acute angle to the longitudinal axis of tubular member 20.

Outlet aperture 46 communicates through the lowest portion of trough 40, so that all blood will easily drain from the reservoir.

If desired, a calibration strip having volume indication markings may be provided on an outer wall of the reservoir so that, at a minimum blood level, blood volumes as small as 25 or 50 cc. can be measured.

A mass of conventional blood defoaming sponge 23 is positioned within tube 20.

At the upper end of reservoir 10, inlet members are defined, being of a configuration similar to that of the previously described patent application of Crockett, et al.

An aperture is defined by a sleeve member 54 which passes through casing 12 and in which is fitted luer lock connector 56 for the addition of supplemental medication when desired. The connector 56 may be of conventional design.

Vent tube 58 may be provided with a closable rubber vent cap 60. If desired, a porous, hydrophobic material may be placed in vent tube 58, to filter out any contamination, while permitting the flow of gas into and out of the reservoir.

A port tube (not shown) may also be present to be used as a connection to a vacuum pump, if desired.

Positioned within sleeve 26 is a molded inlet assembly 62, which is also of a design similar to the cited Crockett, et al. application, including three inlet aperture tubes 66.

In accordance with this invention, the conventional blood defoaming sponge 23 positioned in the interior of tube 20 may be supplemented with a second blood defoaming means, which constitutes a generally tubular mass of conventional blood defoaming sponge material 68 such as silicone coated metal turnings, positioned about the exterior of tube 20. Second blood defoaming means 68 is retained in its position by means of a tubular coarse-weave fabric cover 70, which is retained at its ends in a manner similar to the retention of tubular filter 35. The weave of tubular cover 70 may be coarse enough (e.g., an aperture size on the order of 1/16 or 1/32 inch) to allow any small bubbles outside of the cover 70 to pass back into the area occupied by second defoaming means 68 to be dissipated. Cover 70 may, for example, be a knit material. This provides an advantage to the device of this invention, since the presence of fine weave filter member 35 has hitherto generally prevented the passage of such bubbles back into the interior of tube 20 for dissipation.

Accordingly, blood enters the device through an inlet port 66, spilling through the first defoaming means 23 and then passing out of tube 20 through fine weave filter member 35. Any large bubbles are prevented from passage by the presence of fine weave filter 35. Any small bubbles which remain pass through the second defoaming means 68 in the absence of larger bubbles. Blood and bubbles external to the outer coarse-weave retainer member 70 are free to pass relatively unhindered back to the second defoaming sponge 68, which tends to increase the removal rate of such fine bubbles.

Blood is then withdrawn through outlet 46, with the sloping trough 40 serving to facilitate the complete drainage thereof.

The above has been offered for illustrative purposes only, and is not to be viewed as limiting the invention of this application, which is as defined in the claims below.

That which is claimed is:

1. A blood reservoir which comprises a rigid casing, a perforated tubular member positioned within said casing and extending between the ends thereof, inlet aperture means positioned at the upper end of said reservoir in communication with the bore of said tubular member to provide fluid communication from the exterior to said bore, an outlet aperture positioned adjacent the bottom of the casing exterior to the tubular member, and gas venting means, the improvement comprising, in combination: first and second blood defoaming means carried by said perforated tubular member, said second blood defoaming means being positioned about the exterior of said first blood defoaming means, and tubular blood filter means positioned between said first and second blood defoaming means, said tubular filter means being hydrophilic in nature and being of fine-weave construction to retain larger bubbles to prevent their passage through the filter means while permitting microbubbles to so pass through the filter means, whereby the second defoaming means exhibits improved defoaming action for removal of the microbubbles.

2. The blood reservoir of claim 1 in which said second blood defoaming means are enclosed in a tubular, coarse-weave cover capable of allowing small bubbles outside of said cover to pass therethrough into contact with the second blood defoaming means.

3. The blood reservoir of claim 1 in which said tubular, fine-weave filter member has a pore size of 120 to 130 microns.

4. The blood reservoir of claim 1 in which said tubular filter member is made of nylon.

5. The blood reservoir of claim 1 in which said first defoaming means is carried in the bore of said tubular member.

6. The blood reservoir of claim 1 in which said second defoaming means is carried about the exterior of said tubular member.

7. In a blood reservoir defining means for carrying blood defoaming means and for passing blood therethrough, the improvement comprising, first and second blood defoaming means positioned adjacently to each other with the first blood defoaming means being positioned upstream of the second blood defoaming means relative to the normal blood flow path, and blood filter means positioned between said first and second blood defoaming means, said filter means being hydrophilic in nature and being of fine-weave construction to retain larger bubbles to prevent their passage through the filter means, while permitting microbubbles to so pass through the filter means, whereby the second defoaming means exhibits improved defoaming action for removal of the microbubbles in blood passed to it from the first blood defoaming means.

8. The method of removing an improved percentage of bubbles from blood which includes the steps of passing blood through first blood defoaming means; passing said blood immediately thereafter through blood filter means made of a generally hydrophilic material and a fine-weave construction to retain larger bubbles to prevent their passage through the filter means, and then passing said filtered blood through second blood defoaming means to remove microbubbles remaining in the blood in an environment which is essentially free of said larger bubbles.

9. The method of claim 8 which includes the step of allowing blood in a chamber exterior to said second blood defoaming means to pass through a relatively coarse-weave cover enclosing said second blood defoaming means, whereby bubbles present in the blood downstream from said blood defoaming means may enter into contact with the second blood defoaming means for removal thereof by back flowing through said coarse-weave cover.

* * * * *